(12) United States Patent
Bertrand

(10) Patent No.: US 7,587,934 B2
(45) Date of Patent: Sep. 15, 2009

(54) METHOD OF QUANTIFYING THE UTILIZATION OF A MAXIMUM GRIP POTENTIAL OF A TIRE

(75) Inventor: David Bertrand, Besançon (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 12/012,404

(22) Filed: Feb. 1, 2008

(65) Prior Publication Data

US 2008/0190187 A1 Aug. 14, 2008

(30) Foreign Application Priority Data

Feb. 2, 2007 (FR) .................................. 07 53025

(51) Int. Cl.
*G01M 17/02* (2006.01)
(52) U.S. Cl. ..................................... 73/146; 152/152.1
(58) Field of Classification Search ........ 73/146–146.8; 152/152.1
See application file for complete search history.

(56) References Cited

U.S. PATENT DOCUMENTS

2003/0056579 A1* 3/2003 Poulbot et al. ................ 73/146
2004/0158414 A1 8/2004 Bertrand
2005/0065699 A1 3/2005 Bertrand
2005/0188756 A1* 9/2005 Morikawa .................... 73/146
2008/0202657 A1* 8/2008 Hammel .................. 152/152.1
2008/0245456 A1* 10/2008 Spetler .................... 152/209.1

FOREIGN PATENT DOCUMENTS

WO    WO 2006/010680    2/2006

OTHER PUBLICATIONS

Search Report dated Oct. 10, 2007 issued for the corresponding French Patent Application No. 0753025.

* cited by examiner

*Primary Examiner*—Andre J Allen
(74) *Attorney, Agent, or Firm*—Cohen Pontani Lieberman & Pavane LLP

(57) ABSTRACT

A method of quantifying the utilization of a maximum grip potential of a tire running on the ground. At two distinct azimuth angles, at least two respective values are determined for a differential extension of the tread of the tire or for a shear of the tread that is homogeneous with said differential extension. The utilization is quantified with the help of a function of the two determined values.

10 Claims, 6 Drawing Sheets

METHOD OF QUANTIFYING THE UTILIZATION OF A MAXIMUM GRIP POTENTIAL OF A TIRE

RELATED APPLICATION

This application claims the priority of French patent application no. 07/53025 filed Feb. 2, 2007, the content of which is hereby incorporated by reference.

FIELD OF THE INVENTION

The present invention relates to a method of quantifying the utilization of a maximum grip potential of a tire running on ground, and also to a tire.

BACKGROUND OF THE INVENTION

The grip potential μ of a tire is defined, at a given instant, as being the ratio of the resultant of the longitudinal and lateral forces over the resultant of the vertical forces:

$$\mu = \frac{\sqrt{F_x^2 + F_y^2}}{F_z}$$

At a given instant, the maximum grip potential $\mu_{max}$ of the tire on the ground is also defined as being the maximum value that the grip potential μ can take on. This maximum grip potential $\mu_{max}$ depends on several factors including the nature of the ground (or the road) or its state of wear, the temperature of the ground and of the tire, or indeed weather factors involving, for example, the presence of water or snow on the ground.

The utilization percentage $P_u$ of the maximum grip potential $\mu_{max}$ of the tire is then defined by the following formula:

$$P_u = \frac{\mu}{\mu_{max}} \cdot 100$$

This utilization percentage $P_u$ corresponds to the percentage of the grip potential that is actually being used relative to the maximum grip potential. This value varies over the range from 0 to 100%. Naturally, the closer this value is to 100%, the greater the risk of the tire losing grip. Thus, the utilization percentage $P_u$ serves to quantify utilization of maximum grip potential.

It is advantageous to quantify in real time the extent to which the maximum grip potential of each tire of a motor vehicle is being utilized in order to determine whether or not one of the tires is close to losing its grip with the ground. This information concerning tire grip can be transmitted to the driver of the vehicle so as to adapt driving accordingly, or to an electronic device for controlling the road holding of the vehicle.

Document WO 03/066400 discloses that the maximum grip potential $\mu_{max}$ of a tire depends in particular on the following parameters:
- the driving or braking force applied to the tire;
- the lateral thrust force applied to the tire;
- the load carried by the tire; and
- the self-alignment torque, i.e. the moment about a vertical axis that is exerted by the tire.

These various force parameters can be measured by means of sensors carried by the tire, in particular by means of sensors that measure the forces to which the walls or the rubbing strips of the tire are subjected.

The maximum grip potential can be deduced from those force measurements by training an approximation function, e.g. by training the weights of a neural network.

That known method of estimation turns out to be particularly complex to implement and requires complicated calibration of the tire and also close monitoring of variation in its parameters over time. As a result that method is expensive to implement in practice.

OBJECTS AND SUMMARY OF THE INVENTION

One object of the invention is to provide a method of quantifying the utilization of the maximum grip potential of a tire running on ground, which method is particularly simple to implement.

To this end, one aspect of the invention is directed to a method of quantifying the utilization of a maximum grip potential of a tire running on the ground, the method comprising the following steps:
- determining at least two values for a differential extension of the tread of the tire or for a shear of the tread that is homogeneous with said differential extension, respectively at two distinct azimuth angles; and
- quantifying said utilization with the help of a function of these two determined values.

By means of the invention, the utilization of the maximum grip potential of the tire is quantified in a manner that is particularly simple and fast. The values used for making this estimate are very easy to measure by means of a conventional sensor incorporated in the tread of the tire, and the utilization function makes use of simple algebraic operators such as addition or division. Furthermore, the method makes it possible to obtain directly a measure that quantifies said utilization, without it being necessary to calculate beforehand the maximum grip potential of the tire, thereby achieving a considerable reduction in the resources needed to perform said quantification.

The result of the quantification may, for example, be given as a number lying in the range 0 to 1, or else as a percentage.

A quantification method according to an embodiment of the invention may also include one or more of the following characteristics.

The two azimuth angles define an acute-angle sector containing the contact area of the tread with the ground. The deformation of the tire is due essentially to contact with the ground. Consequently, it is preferable for the extension or shear values used for quantifying said utilization to be determined for azimuth angles that are close to the contact area so that these values are influenced by the tire making contact with the ground and thus by the grip conditions of the tire.

The angular sector is about 50°. Quantification is of better quality if the values are measured away from the contact area (so as not to be subjected to the influence of the surface state of the road), but as close as possible to the contact area (in order to maximize the influence of the grip conditions of the tire on the ground). It has been found that an angular sector of about 50° centered on the contact area is optimum for satisfying these two criteria.

The value of the differential extension or of the shear, as determined at a given azimuth angle θ is written Δ(θ), and said utilization is quantified with the help of a value S that is defined as follows:

$$S = \frac{((\Delta(\theta_1) - \Delta(\theta_2)) - O - P_{slip} \cdot (\Delta(\theta_1) + \Delta(\theta_2)))}{(P_{grip} - P_{slip}) \cdot (\Delta(\theta_1) + \Delta(\theta_2))}$$

where $P_{grip}$, $P_{slip}$, and O are predetermined constants, and $\theta_1$ and $\theta_2$ are the two distinct azimuth angle values.

The value of this quotient is directly connected to the utilization being made of the maximum grip potential. This calculation, which can be performed particularly fast, thus makes it possible to obtain a value that can be interpreted very easily since it varies over the range 0 to 1.

In the above formula, $P_{slip}=0$. Generally $P_{slip}$ can be ignored, thereby simplifying the formula for calculating S.

The quantification of said utilization is also a function of a length of the tread contact area with the ground.

When the determined values are shear values, each shear value of the tread is determined substantially in an equatorial plane of the tread.

The differential extension corresponds to the difference between two extension values of the tread measured substantially symmetrically about an equatorial plane of the tire.

The measured extension values are extension values in a direction that is substantially circumferential relative to the tire.

The extension or the shear of the tread is determined respectively by means of at least one extension or shear sensor, preferably implanted between a carcass ply and inside rubber of the tire or on a face of the inside rubber that is in contact with the air inside the tire.

Said utilization is quantified with the help of a function of the difference between the two determined values, and of the sum of said two determined values.

Another aspect of the invention is directed to a tire including at least two extension sensors and wherein the extension sensors are carried by the tread of the tire and are arranged to measure the extension of two portions of the tread for a given azimuth angle.

In the state of the art, tires are fitted with force sensors disposed in each of the walls of a tire. For the sensors to be powered electrically, it is necessary to have wires inside the tire interconnecting its two walls. By means of an embodiment of the invention, the two sensors are placed on the tread. This makes it possible to integrate both sensors within a single module that is disposed on the tread and that includes an electrical power supply that is fully integrated.

DETAILED DESCRIPTION OF THE DRAWINGS

Figure 1:
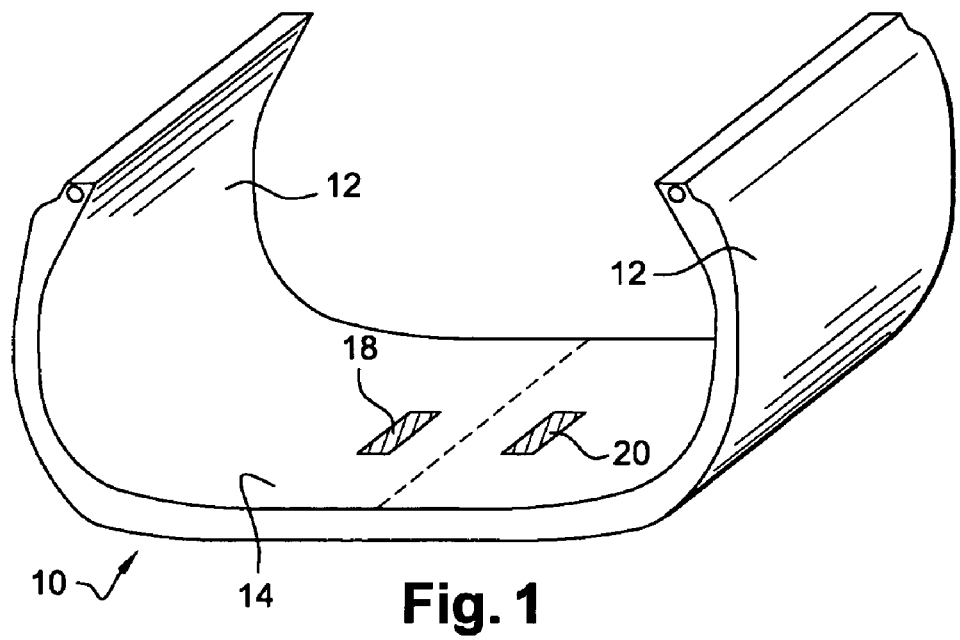
FIG. 1 is a perspective diagram of a tire according to an embodiment of the invention, fitted with two extension sensors.

FIG. 1 shows a tire given overall reference 10, having two walls 12 and a tread 14. The portion of the tread 14 in contact with the ground is referred to as the contact area 16. The contact area 16 is visible in FIG. 13, which is described below.

The tire 10 is provided with two extension sensors 18 and 20 arranged on the tread 14 in such a manner as to measure the extension of the tread at two points in a substantially circumferential direction of the tire.

The two extension sensors 18 and 20 are positioned relative to the tire 10 at the same azimuth angle. As can be seen in FIG. 1, the two sensors 18 and 20 are disposed substantially symmetrically about an equatorial plane of the tire 10, e.g. at 30 millimeters (mm) from said plane. This characteristic is nevertheless optional when implementing the invention.

A tire is considered while it is rotating. At a given instant, the azimuth angle at which the two sensors 18 and 20 are to be found relative to a frame of reference external to the tire is written to $\theta$. The azimuth angle $\theta=180°$ corresponds to the sensors 18 and 20 passing vertically under the axis of rotation of the tire.

For a given azimuth angle $\theta$, a differential extension $\Delta(\theta)$ is defined as follows:

$$\Delta(\theta) = \epsilon_1(\theta) - \epsilon_2(\theta)$$

The value $\Delta(\theta)$ corresponds to the difference between the extension $\epsilon$ measured by the two extension sensors 18 and 20. It is thus representative of the state of bending in the plane of the tread 16 at azimuth angle $\theta$.

Two azimuth angles defining an acute angular sector containing the contact area 16 of the tread 14 on the ground are written $\theta_e$ and $\theta_s$. Azimuth angle $\theta_e$ is selected to be at the point of entry into the contact area and azimuth angle $\theta_s$ is selected at the exit point from the contact area. By way of example, the selected values are $\theta_e=156°$ and $\theta_s=204°$, such that the angular sector is of the order of 50°.

In the description below, a tire running on the ground is considered as being subjected to two different types of stress:

a first type of stress corresponding to normal running on ground providing perfect grip. This stress is referred to as "grip stress"; and a second type of stress corresponds to running on ground having characteristics that are selected such that the forces generated correspond to the grip limit. This stress is referred to as "slip stress".

Two these two kinds of stress correspond to extreme circumstances and stress as really encountered is usually intermediate therebetween.

Use is made below more particularly of the following values $\Delta_e=\Delta(\theta_e)$, $\Delta_s=\Delta(\theta_s)$, $\Delta_e+\Delta_s$ and $\Delta_s-\Delta_e$, and to the way in which they vary as a function of the forces applied to the tire 10 under three circumstances.

Figure 2:
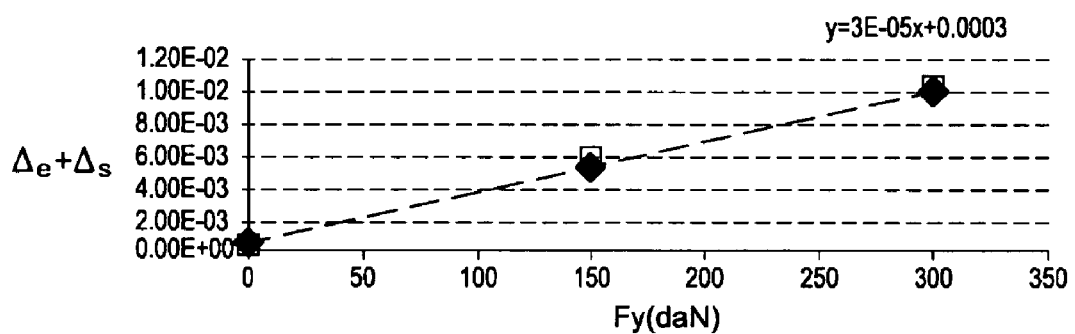
FIGS. 2 and 3 are graphs showing the variation respectively in $\Delta e + \Delta s$ and $\Delta s - \Delta e$ as a function of a lateral force.

First Circumstance: Tire Subjected Solely to a Lateral Force Fy and to a Constant Vertical Load FIG. 2 is a graph showing the values taken by $\Delta_e+\Delta_s$ for a given load as a function of the lateral thrust Fy. In these figures, solid lozenges correspond to grip stress and open squares correspond to slip stress. It can be seen from the graph that independently of the type of stress, there is a simple affine type relationship between $\Delta_e+\Delta_s$ and the value of the lateral thrust Fy.

Figure 3:
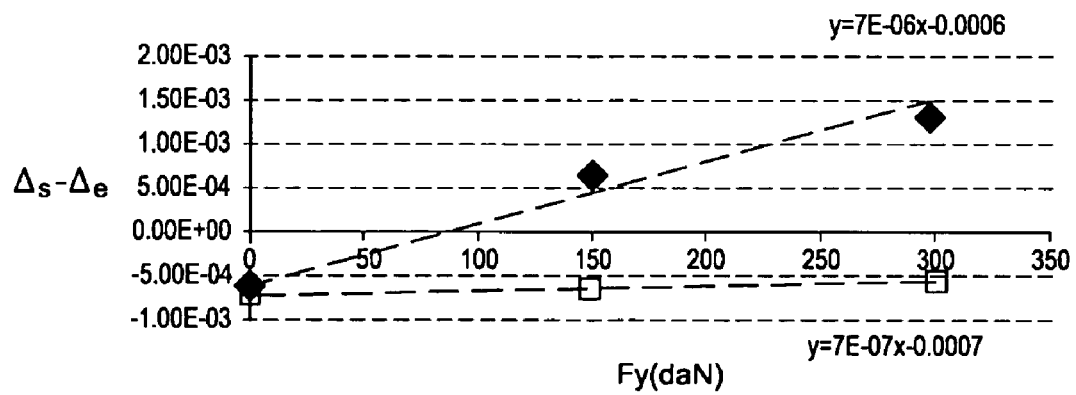

FIG. 3 shows values of $\Delta_s-\Delta_e$ for a given load as a function of the lateral thrust Fy. It can be seen that an affine relationship exists for the two magnitudes, both for grip stress and for slip stress, but that the gradient of this relationship depends on the type of stress.

Figure 4:
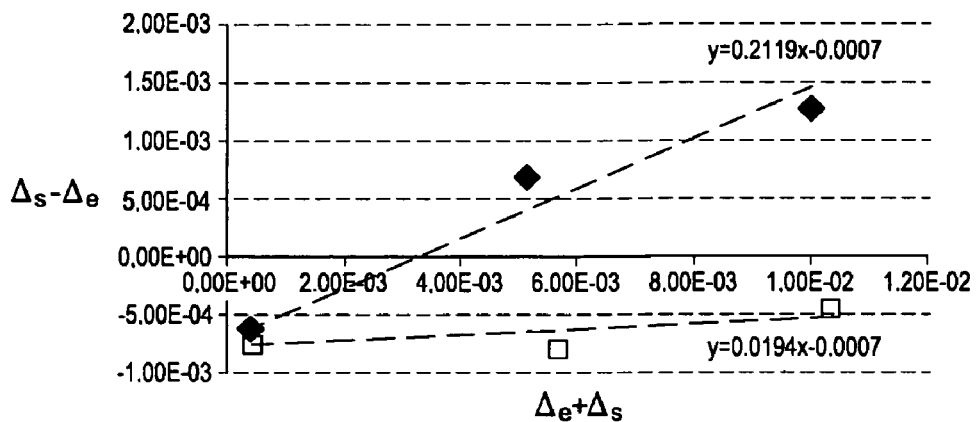
FIGS. 4 and 5 are graphs showing how $\Delta s - \Delta e$ varies as a function of $\Delta s + \Delta e$.
Figure 5:
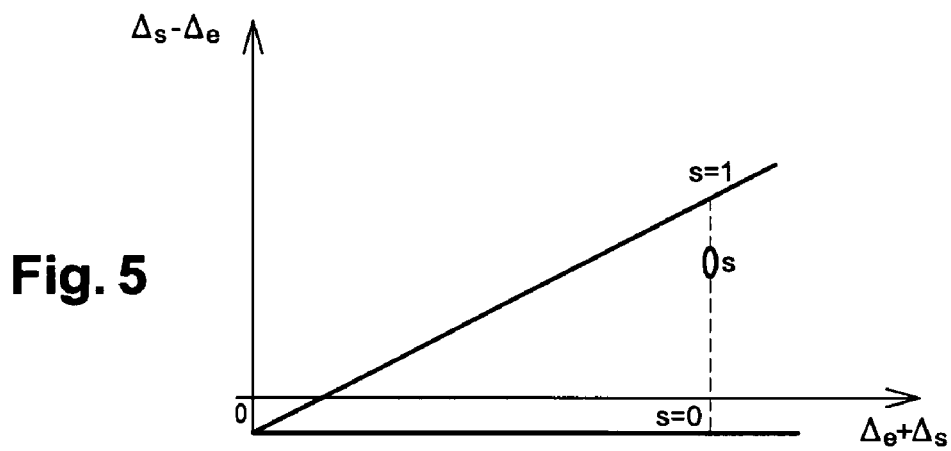

By combining the results given in FIGS. 2 and 3, it is possible to form FIG. 4 that shows the relationship between $\Delta_s-\Delta_e$ and $\Delta_e+\Delta_s$ depending on the type of stress. It can be seen that for a given type of stress, these two values are associated by a proportionality coefficient. This is represented by two straight lines plotted in FIG. 4.

During real stress, the points representing the pairs ($\Delta_e+\Delta_s$, $\Delta_s-\Delta_e$) lie in the space between the two straight lines shown in FIG. 4 that correspond to two extreme kinds of stress. A value S is then defined such that:

S=0 when the point corresponding to the current pair is situated on the straight line representing slip stress; and S=1 when the point corresponding to the current pair is situated on the straight line representing grip stress.

S can then be written as follows:

$$S = \frac{(\Delta_s - \Delta_e) - (\Delta_s - \Delta_e)_{slip}}{(\Delta_s - \Delta_e)_{grip} - (\Delta_s - \Delta_e)_{slip}}$$

Using the notation O for the ordinate value at the origin of the two straight lines, $P_{grip}$ for the slope of the straight line corresponding to grip stress, and $P_{slip}$ for the slope corresponding to slip stress, the expression for S becomes:

$$S = \frac{(\Delta_s - \Delta_e) - O - P_{slip} \cdot (\Delta_s + \Delta_e)}{(P_{grip} - P_{slip}) \cdot (\Delta_s + \Delta_e)}$$

In a simplified version in which the slope $P_{slip}$ is ignored, the following expression is obtained:

$$S = \frac{(\Delta_s - \Delta_e) - O}{P_{grip} \cdot (\Delta_e + \Delta_s)}$$

Thus, calculating S and comparing it with the values 0 and 1 makes it possible to determine whether the stress on the tire is closer to perfect grip stress or to slip stress, and to quantify how close. By calculating the value S, it is thus possible to quantify utilization of the maximum grip potential of the tire while it is running on the ground.

To summarize, calculating the value S consists in determining at least two values $\Delta_e$ and $\Delta_s$ for differential extension of the tread of the tire at two distinct azimuth angle values $\theta_e$ and $\theta_s$, and in calculating the value of S so as to quantify the extent to which the maximum potential is being utilized.

Second Circumstance: Tire Also Subjected to Variations in Load

The above reasoning assumes that the tire is subjected solely to a given vertical load and to a given lateral thrust.

In reality, the load borne by the tire varies continuously. It is therefore necessary to take account of variations in the load borne by the tire in the method used for calculating S in order to improve the model.

Figure 6:
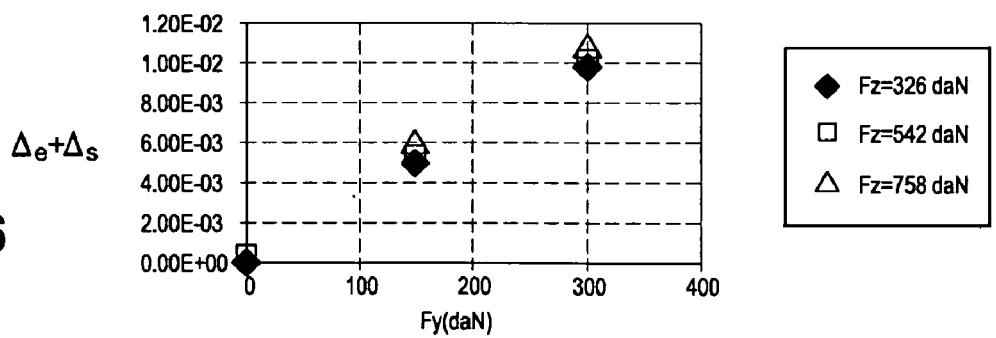
FIGS. 6 and 7 show respectively how $\Delta s + \Delta e$ and $\Delta s - \Delta e$ vary as a function of lateral force, for different vertical loads.
Figure 7:
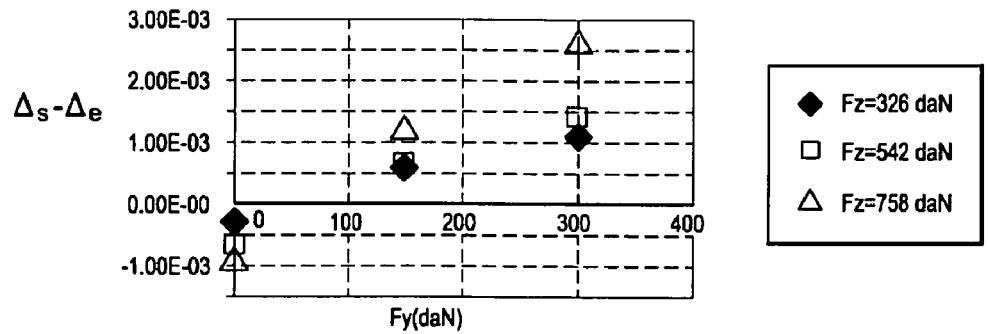

FIGS. 6 and 7 show the effects of varying the load borne by the tire on the values of $\Delta_e+\Delta_s$ and $\Delta_s-\Delta_e$. Load variation and thus deflection have no significant effect on the relationship between $\Delta_e+\Delta_s$ and lateral thrust (FIG. 6). In contrast, FIG. 7 shows that load does have an influence on the relationship between $\Delta_s-\Delta_e$ and lateral thrust.

In order to introduce a correction into the affine relationship connecting the $\Delta_s-\Delta_e$ to $\Delta_e+\Delta_s$ as a function of the deflection of the tire, a criterion is defined that makes it possible to estimate the length of the contact area. This value can be used for parameterizing the slope $P_{grip}$ and the ordinate at the origin O.

A value $\Sigma(\theta)$ is then defined as follows:

$$\Sigma(\theta)=\epsilon_1(\theta)+\epsilon_2(\theta)$$

The value $\Sigma(\theta)$ is characteristic of the radius of curvature of the tread. When the radius of curvature increases, the signals from the two extension sensors both increase by the same amount. Consequently, during a revolution of the wheel, the value $\Sigma(\theta)$ presents two characteristic points $\theta_e$ and $\theta_s$ corresponding respectively to the sensors entering and exiting the contact area. A criterion that is characteristic of the length of the contact area is then defined as follows: $L_{ca}=\theta_s-\theta_e$. Under such circumstances, the criterion is expressed in degrees and not in meters.

Figure 8:
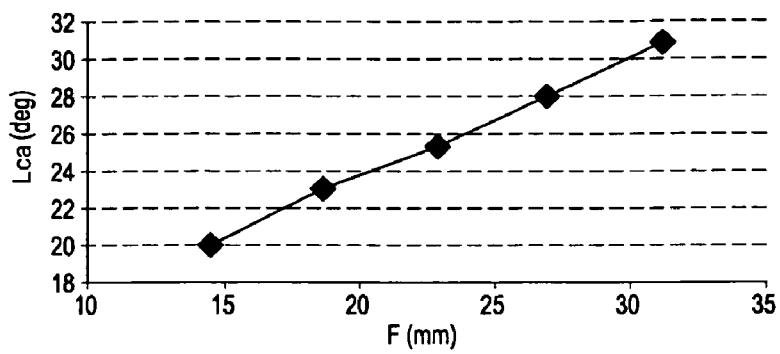
FIG. 8 shows how the length of the contact area varies as a function of the deflection of the tire.

FIG. 8 shows how the length of the contact area varies as a function of the deflection of a tire as obtained for different loads. The length of the contact area is manifestly proportional to the deflection.

Figure 9:
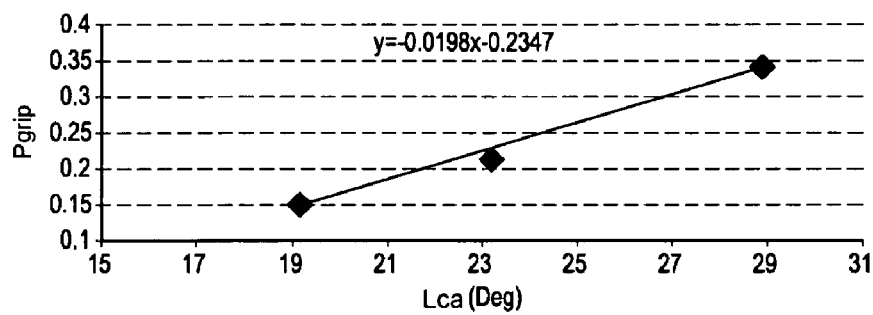
FIGS. 9 and 10 are graphs showing how the parameters P and O vary as a function of the length of the contact area.
Figure 10:
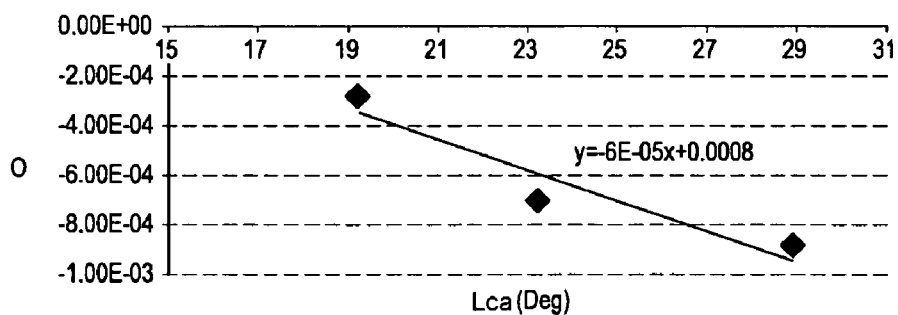

FIGS. 9 and 10 show how $P_{grip}$ and O vary as a function of $L_{ca}$, as defined above. These two graphs show that it is possible to associate $P_{grip}$ and O simply with $L_{ca}$, e.g. in affined manner. $P_{grip}$ and O are thus defined as follows:

$$P_{grip}=a_p L_{ca}+b_p$$

$$O=a_O L_{ca}+b_O$$

Naturally, the length of the contact area can be measured using data other than the data provided by the extension sensors.

Third Circumstance: Tire Also Subjected to a Driving or Braking Torque

While in use on a vehicle, a tire is also used to transmit a driving or braking torque. In this respect, it is subjected to deformations that can interact with the above-described operation. As shown below when describing FIGS. 15 and 16, the effect of driving or braking torque gives rise to difference between entry to and exit from the contact area.

Figure 11:
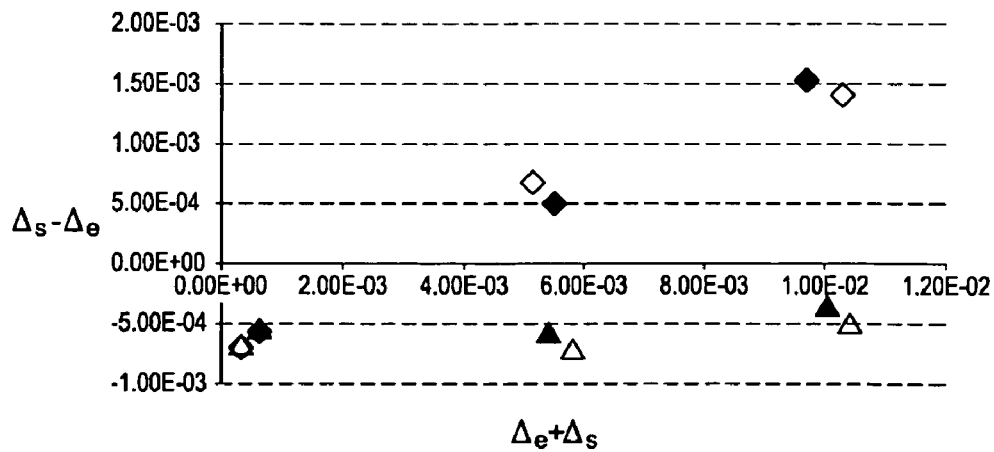
FIG. 11 shows how the values of $\Delta s + \Delta e$ and $\Delta s - \Delta e$ vary when a driving torque is applied to the tire.

FIG. 11 shows how the values $\Delta_e+\Delta_s$ and $\Delta_s-\Delta_e$ vary, firstly without driving toque (open marks), and secondly with driving torque having a magnitude of about 45 meter-decanewtons (m·daN) (solid marks). It can be seen that the model presents very little sensitivity to the effects generated by a driving or braking torque. Thus, the model as described above does not need to be modified in order to take account of a driving torque effect.

The above description of the method of the invention thus shows that determining the value S serves in particularly satisfactory manner to quantify the extent to which the maximum grip potential of the tire is being utilized. This determination takes account of the various forces applied to the tire, in particular the lateral thrust force, the vertical load, and also drive and braking torque. In addition, the value of S may also vary a little as a function of the pressure to which the tire is inflated and of its camber angle.

It should be observed that the description above relies on determining a differential extension by means of two extension sensors carried by the tread of the tire. Nevertheless, it would not go beyond the ambit of the invention to use a single shear sensor disposed in the equatorial plane of the tire in order to determine a shear in the tread. The shear in the equatorial plane of the tire is uniform at differential extension $\Delta(\theta)$. Consequently, the formulae for calculating the value of S remain valid in the event of it being a shear that is determined, since it suffices to replace the differential extension value $\Delta(\theta)$ by a shear value as measured by means of a shear sensor.

Examples of Signals Delivered by the Extension Sensors

By way of illustration, the description below shows how a tire deforms when subjected to various forces. It also shows the influence of these various deformations on the signals delivered by the two extension sensors carried by the tread of the tire.

Consideration is given to the tire shown in FIG. 1 and provided with two extension sensors 18 and 20 positioned respectively at +30 mm and at −30 mm from the equatorial plane of the tire. When the sensors measure extension, the value of the signal increases, and when they measure compression, the value of the signal decreases.

Figure 12:
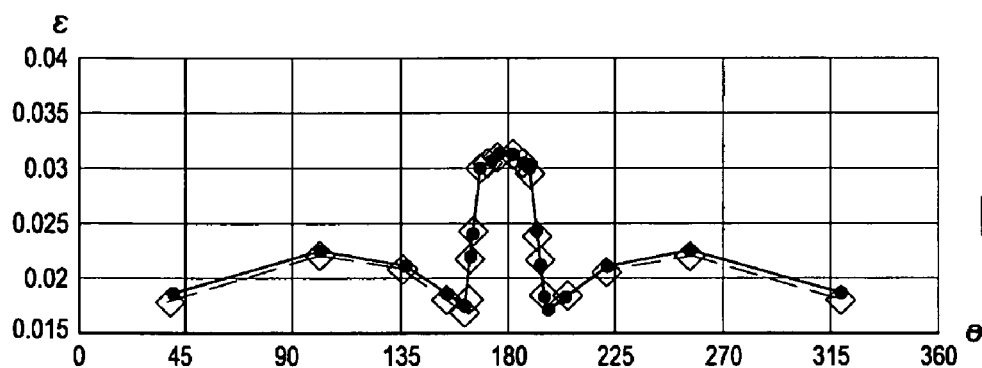
FIG. 12 is a graph of the signals delivered by the two extension sensors under normal conditions of use.

FIG. 12 shows the signals generated by the two sensors over one revolution of the wheel (i.e. during rotation through 360°) when the tire is subjected to a vertical load of 542 decanewtons (daN). The signal delivered by the first sensor is represented by dots and by a continuous line, while the signal delivered by the second sensor is represented by lozenges and by a discontinuous line.

It can be seen that the signals delivered by the two sensors are substantially identical. These two signals differ only in the non-isotropic effects of the materials constituting the tire.

It can be seen that in the vicinity of azimuth angle 180°, the signals delivered by the sensors increase. This is due to the sensors passing into the contact area of the tire with the ground. While the tread is in contact with the ground, it deforms and its radius of curvature increases. In fact, its radius of curvature tends towards infinity since the tread flattens. This increase in radius of curvature then causes the tread to stretch and therefore stretches the extension sensor.

Figure 13:
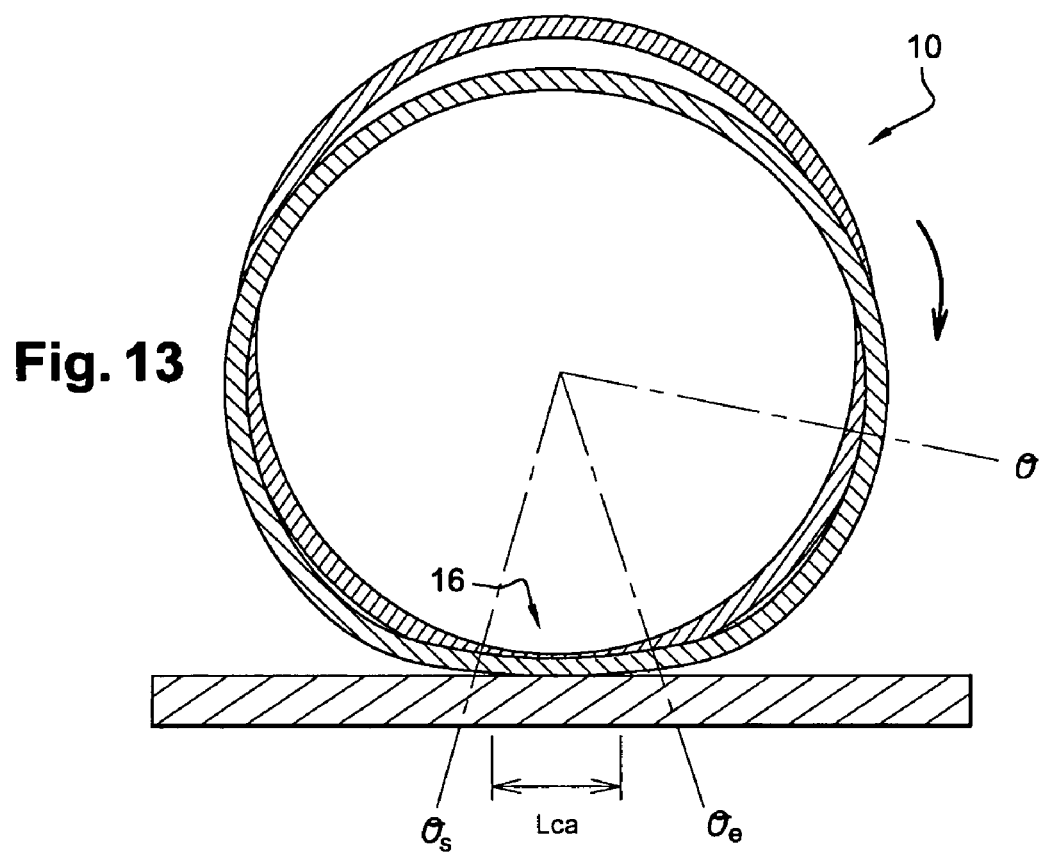
FIGS. 13 and 14 are respectively a diagram of a tire subjected to a vertical force and a graph of the signals supplied by the extension sensors of the tire.

This flattening of the contact area is shown in FIG. 13 which shows two tires, one (in gray) that is not subjected to any vertical load, and the other (in black) that is subjected to a vertical load. The deformation of the tread creates a contact area (16) of length $L_{ca}$.

Figure 14:
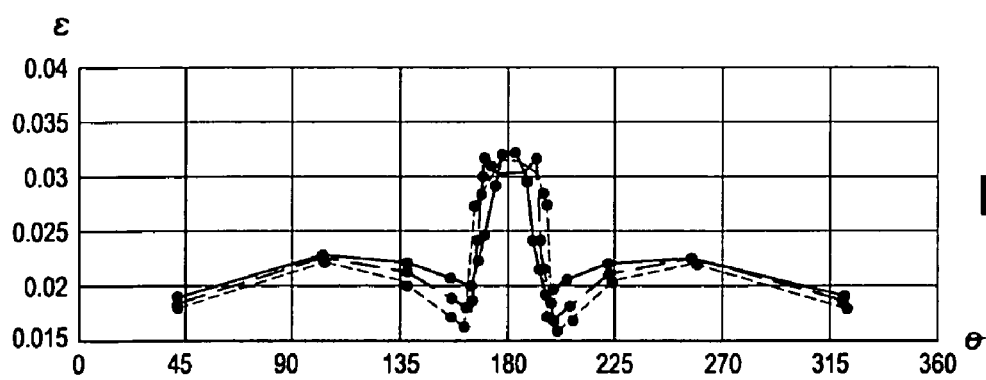

The greater the vertical force applied to the tire, the more the tire flattens and thus the greater the length of the contact area. FIG. 14 shows the effect of variation in deflection on the appearance of the measurement signals. Variation in deflection is obtained by varying the vertical load. FIG. 14 shows how a signal as delivered by a sensor during a revolution of the tire varies for three given load values: the continuous curve corresponds to a load of 326 daN, the dotted curve to a load with a value of 542 daN, and the chain-dotted curve to a load with a value of 758 daN.

From these signals, it can be seen that the length of the zone corresponding to the contact area increases with increasing deflection. It can also be seen that the values of the signal on entry and exit to or from the contact area decrease with increasing deflection, which means that the radius of curvature is smaller.

Figure 15:
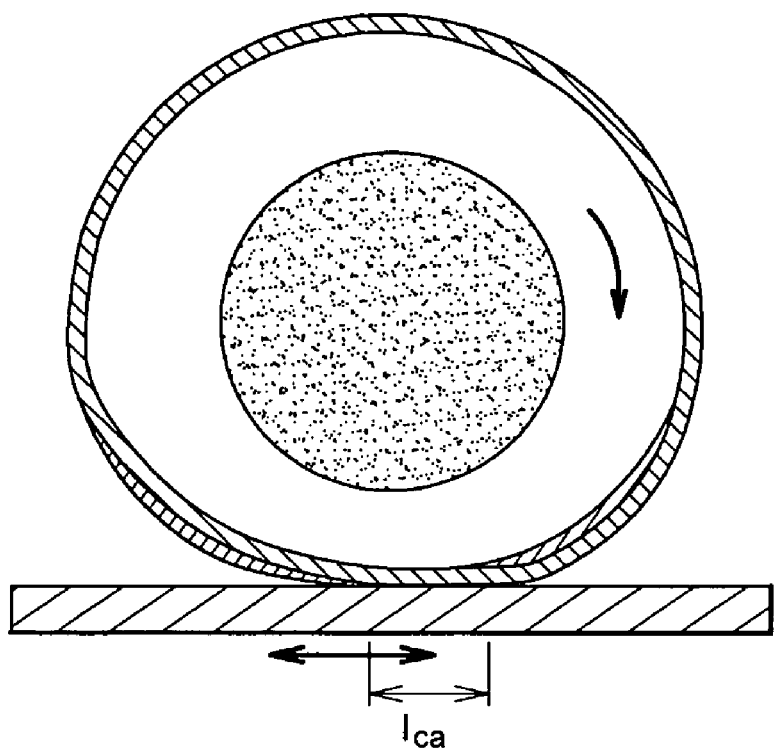
FIGS. 15 and 16 are respectively a diagram of a tire subjected to a driving torque and the graph of the signals delivered by the extension sensors of the tire.
Figure 16:
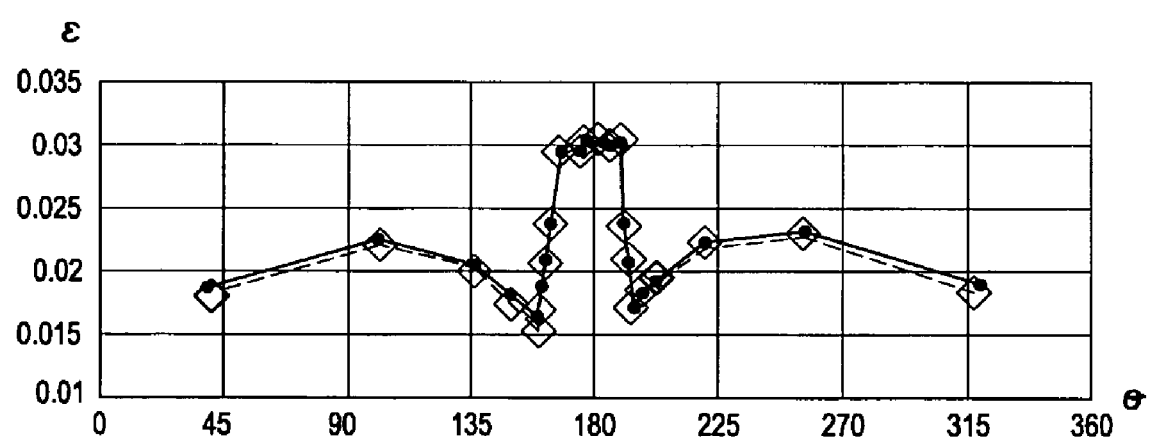

FIGS. 15 and 16 show the effect of driving torque on the tire and on the signals delivered by the extension sensors.

In FIG. 15, it can be seen that when the tire is subjected to a driving torque, the contact area of the tread with the ground is shifted forwards.

This shift can also be deduced from the graph of FIG. 16 that shows how the signals delivered by the sensors vary when the tire is additionally subjected to a driving torque that generates a longitudinal force of 150 daN. From this graph, it can be seen that the presence of a driving torque gives rise to the following effects:

a reduction in the extension measured on entry into the contact area and an increase in the extension measured on exit from the contact area. This is the result of a decrease in the radius of curvature on entry into the contact area and an increase in the radius of curvature on exit from the contact area, as can be seen in FIG. 15; and a small shift of the zone corresponding to the contact area in the forward direction (i.e. towards smaller azimuth angles), which corresponds to a longitudinal offset.

Figure 17:
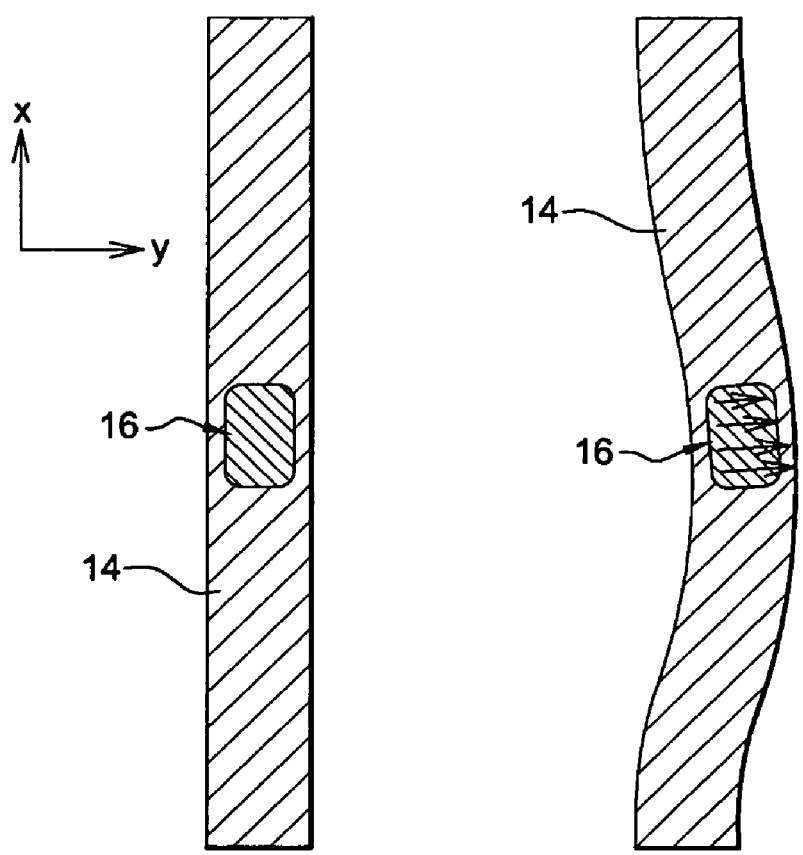
FIGS. 17 and 18 are respectively a diagram of a tire subjected to a side force and a graph showing the signals delivered by the extension sensors of the tire.
Figure 18:
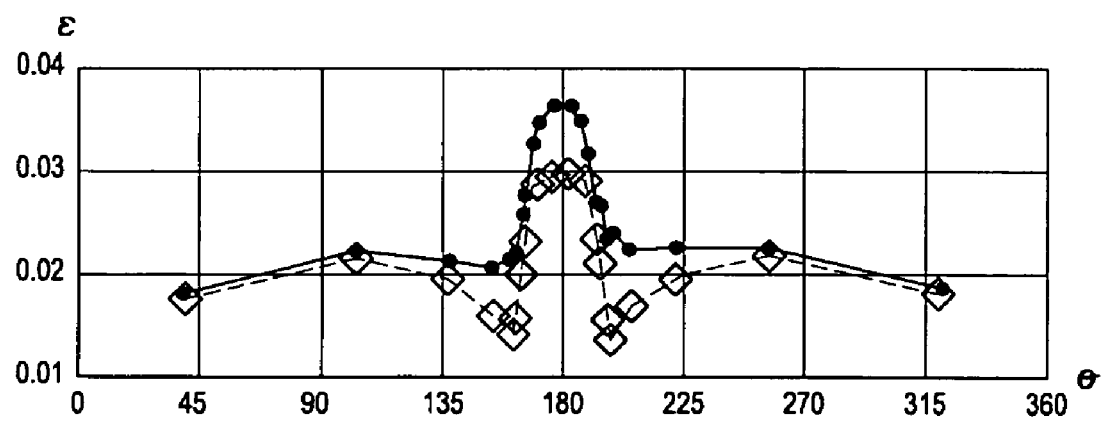

Consideration is now given to circumstances in which the tire is subjected to a lateral force. For this purpose, FIG. 17 shows the trace of the tread of the tire, when not subjected to any lateral force (left-hand figure) and when it is subjected to a lateral force (right-hand figure). The contact area of the tread with the ground is shown on the trace.

When the tire is subjected to a lateral force, the contact area is offset sideways, thereby causing bending in the plane of the tread that is in contact with the ground. In addition, because the shear stresses are not distributed uniformly throughout the contact area, the portion of the tire tread pattern situated at the exit from the contact area is subjected to greater shear than is the portion situated at the entry. This generates a torque about the vertical axis that corresponds to the self-alignment torque. This torque tends to cause the contact area to turn about the vertical axis, with this turning then giving rise to a difference between the bending in the plane of the tread on entry to, and on exit from, the contact area, as can be seen in FIG. 7.

The effects of these deformations on the signals delivered by the sensors can be seen clearly in FIG. 11 in which it is assumed that the tire is subjected to a lateral thrust of 300 daN. The signals can be analyzed as follows:

the lateral thrust applies at a point disposed towards the rear of the contact area relative to the center of the contact area such that the signals delivered by the two sensors differ, particularly within the contact area;

the signal delivered by one of the two sensors presents an amplitude greater than the signal delivered by the other sensor, which is representative of a difference in extension and thus of bending in the plane of the tread of the tire; and finally the difference between the values of the two signals on entry to (156°) and on exit from (204°) the contact area is not the same, which means that there is a difference in bending between entry to and exit from the contact area. As shown above with reference to FIG. 17, this difference in bending is due to the turning of the contact area imposed by the self-alignment torque.

FIGS. 12 to 18 as described above show in particular that because of the way the two extension sensors are positioned in the tread of the tire, it is possible to know accurately the deformation to which the tire is subjected. This deformation is due to the forces applied to the tire, which forces are themselves associated with the grip performance of the tire.

This therefore makes it possible to show why the method of the invention is effective in quantifying the extent to which the maximum grip potential of a tire running on the ground is being utilized, by measuring deformation of the tread.

What is claimed is:

1. A method of quantifying the utilization of a maximum grip potential of a tire running on the ground, comprising the steps of:

determining at least two values for a differential extension of the tread of the tire or for a shear of the tread that is homogeneous with said differential extension, respectively at two distinct azimuth angles; and wherein the value of the differential extension or of the shear, as determined at a given azimuth angle θ is written $\Delta(\theta)$, and said utilization is quantified with the help of a value S that is defined as follows:

$$S = \frac{((\Delta(\theta_1) - \Delta(\theta_2)) - O - P_{slip} \cdot (\Delta(\theta_1) + \Delta(\theta_2)))}{(P_{grip} - P_{slip}) \cdot (\Delta(\theta_1) + \Delta(\theta_2))}$$

where $P_{grip}$, $P_{slip}$, and O are predetermined constants, and $\theta_1$ and $\theta_2$ are the two distinct azimuth angle values.

2. The method according to claim 1, wherein the two azimuth angles define an acute angular sector containing the contact area of the tread with the ground.

3. The method according to claim 2, wherein the angular sector is about 50°.

4. The method according to claim 1, wherein $P_{slip}=0$.

5. The method according to claim 1, wherein the quantification of said utilization is also a function of a length of the contact area of the tread with the ground.

6. The method according to claim 1, wherein, when the determined values are shear values, each shear value of the tread is determined substantially in an equatorial plane of the tread.

7. The method according to claim 1, wherein the differential extension corresponds to the difference between two extension values of the tread measured substantially symmetrically about an equatorial plane of the tire.

8. The method according to claim 7, wherein the measured extension values are extension values in a direction that is substantially circumferential relative to the tire.

9. The method according to claim 1, wherein the extension or the shear of the tread is determined respectively by means of at least one extension or shear sensor, preferably implanted between a carcass ply and inside rubber of the tire or on a face of the inside rubber that is in contact with the air inside the tire.

10. The method according to claim 1, wherein said utilization is quantified with the help of a function of the difference between the two determined values, and of the sum of said two determined values.

* * * * *